(12) United States Patent
Rose et al.

(10) Patent No.: US 10,117,817 B2
(45) Date of Patent: *Nov. 6, 2018

(54) COMPOSITION AND PROCESS FOR SEMI-PERMANENT STRAIGHTENING OF THE HAIR

(71) Applicant: Kao Corporation, Tokyo (JP)

(72) Inventors: Burkhard Rose, Darmstadt (DE); Jonathan Wood, Weinheim (DE); Manfred Dürr, Münster (DE); Jörg Schneider, Griesheim (DE); Peter Bauer, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/770,585

(22) PCT Filed: Sep. 16, 2013

(86) PCT No.: PCT/EP2013/069124
§ 371 (c)(1),
(2) Date: Aug. 26, 2015

(87) PCT Pub. No.: WO2014/131469
PCT Pub. Date: Sep. 4, 2014

(65) Prior Publication Data
US 2016/0000671 A1  Jan. 7, 2016

(30) Foreign Application Priority Data

Feb. 28, 2013 (EP) .................................. 13157226

(51) Int. Cl.
| | | |
|---|---|---|
| *A61Q 5/04* | (2006.01) | |
| *A61K 8/36* | (2006.01) | |
| *A61K 8/365* | (2006.01) | |
| *A61Q 5/06* | (2006.01) | |
| *A61K 8/73* | (2006.01) | |
| *A61K 8/81* | (2006.01) | |
| *A45D 2/00* | (2006.01) | |
| *A45D 7/06* | (2006.01) | |
| *A61K 8/04* | (2006.01) | |
| *A61K 8/06* | (2006.01) | |
| *A61K 8/31* | (2006.01) | |
| *A61K 8/33* | (2006.01) | |
| *A61K 8/34* | (2006.01) | |
| *A61K 8/89* | (2006.01) | |
| *A61K 8/891* | (2006.01) | |
| *A61K 8/92* | (2006.01) | |
| *A61Q 5/12* | (2006.01) | |

(52) U.S. Cl.
CPC .............. *A61K 8/36* (2013.01); *A45D 2/001* (2013.01); *A45D 7/06* (2013.01); *A61K 8/042* (2013.01); *A61K 8/06* (2013.01); *A61K 8/31* (2013.01); *A61K 8/33* (2013.01); *A61K 8/342* (2013.01); *A61K 8/365* (2013.01); *A61K 8/73* (2013.01); *A61K 8/731* (2013.01); *A61K 8/817* (2013.01); *A61K 8/8152* (2013.01); *A61K 8/89* (2013.01); *A61K 8/891* (2013.01); *A61K 8/922* (2013.01); *A61Q 5/04* (2013.01); *A61Q 5/06* (2013.01); *A61Q 5/12* (2013.01); *A61K 2800/48* (2013.01); *A61K 2800/5422* (2013.01); *A61K 2800/5424* (2013.01); *A61K 2800/5426* (2013.01); *A61K 2800/5428* (2013.01); *A61K 2800/594* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 2,434,637 A | 10/1949 | Mattocks et al. | |
| 5,609,168 A | 3/1997 | Kischka et al. | |
| 6,106,579 A | 8/2000 | Kunz et al. | |
| 8,513,200 B2 * | 8/2013 | Dixon | A61K 8/042 |
| | | | 514/20.7 |

(Continued)

FOREIGN PATENT DOCUMENTS

| | | |
|---|---|---|
| CN | 102231974 A | 11/2011 |
| EP | 0 685 219 A2 | 12/1995 |

(Continued)

OTHER PUBLICATIONS

XP002703715: Database GNPD Mintel, Database access10n No. 1692744, report of prior sale of "Moroccan Relaxing Treatment with Argan Oil", Jan. 2012.

(Continued)

*Primary Examiner* — Jyothsna A Venkat
(74) *Attorney, Agent, or Firm* — Foley & Lardner LLP

(57) ABSTRACT

The present invention provides a hair straightening composition with improved ease of use and reduced smoke development during the application of a straightening iron. The composition comprises at least one carboxylic acid of the formula (I) in combination with at least one polymeric thickening agent selected from non-ionic, anionic, cationic and amphoteric polymers having a viscosity of at least 500 mPa·s measured at a polymer concentration of 1% by weight, in water and at 20° C. with a Brookfield viscometer: R—CO—COOH Formula (I) In further aspects, the present invention concerns a process for semi-permanent straightening of the hair, utilizing said composition, the use of the composition for straightening hair, and a kit comprising the composition and a straightening iron.

6 Claims, No Drawings

(56) References Cited

U.S. PATENT DOCUMENTS

| | | | | |
|---|---|---|---|---|
| 2004/0180016 | A1* | 9/2004 | Buck | A61K 8/36 |
| | | | | 424/70.2 |
| 2006/0222614 | A1* | 10/2006 | Buck | A61K 8/604 |
| | | | | 424/70.7 |
| 2008/0085251 | A1 | 4/2008 | Shibuya et al. | |
| 2010/0300471 | A1 | 12/2010 | Malle et al. | |
| 2011/0144142 | A1 | 6/2011 | Hu et al. | |
| 2012/0031420 | A1 | 2/2012 | Gormley et al. | |
| 2015/0305469 | A1 | 10/2015 | Paul | |

FOREIGN PATENT DOCUMENTS

| | | | |
|---|---|---|---|
| EP | 0 911 345 A2 | 4/1999 | |
| EP | 2 014 334 A2 | 1/2009 | |
| EP | 2 258 337 A1 | 12/2010 | |
| GB | 1 416 564 A | 12/1975 | |
| JP | H 02-276824 A | 11/1990 | |
| JP | 2005-145890 A | 6/2005 | |
| WO | WO-2009/063042 A1 | 5/2009 | |
| WO | WO 2010/049434 A2 | 5/2010 | |
| WO | WO 2011/104282 A2 | 9/2011 | |
| WO | WO 2012/010351 A2 | 1/2012 | |
| WO | WO-2012/027369 A2 | 3/2012 | |
| WO | WO 2012/105985 A1 | 8/2012 | |
| WO | WO 2014/072479 A2 | 5/2014 | |
| WO | WO 2014/072645 A1 | 5/2014 | |

OTHER PUBLICATIONS

XP002703716: Database GNPD Mintel; Database access1on No. 1892615, report of prior sale of "Luxury Keratin Treatment", Oct. 2012.

XP002715553: Database GNPD Mintel, Database accession No. 1917354, report of prior sale of "Brazilian Keratin Straightening Kit", Dec. 2012.

XP002715458: "Commission Decision of May 8, 1996 establishing an inventory and a common nomenclature of ingredients employed in cosmetic products", Official Journal of the European Communities, L 132/1, Jun. 1, 1996 (Jun. 1, 1996), pp. 1, 139, 141, 169, 222, 279, 384-385, 421, 520, IJRL:http://eurlcx. curopa.eu/LcxUriScrv/LcxlJriServ.do?uri=0.1:L:1996: 132:0001 :0684:EN :PDF [retrieved on Nov. 4, 2013).

XP007906760 : NALCO, data sheet for "MERQUAT Polyquaternium 7 series", Retrieved from the Internet: URL:http://www.nalco.com/pdli'cosmetics/PolvQ7.pdf on Jan. 9, 2009.

XP002715554: Data sheet on "Jaguar C-162", Solvay-Rhodia Product data sheet: E90002010 Sep. 2011 (Sep. 2011), Retrieved from the Internet: URL :http://www.rhodia.com/product-1 iteraturedownload. acti on? doc I d=0901663 680ad70c9&docLanguagc= EN &docTvpe= TDS&output= BINARY&productName=JAGUAR+C+ 162 [retrieved on Oct. 28, 2013).

XP002715555: Sigma-Aldrich Catalog, entry for "Methyl 2-hydroxyethyl cellulose", URL.:http://www. si gmaaldrich.com/ ca ta I og/product/ aldri ch/ 4 3 50 15 ?lang=cn [retrieved on Oct. 29, 2013).

International Search Report and the Written Opinion of the International Searching Authority corresponding to PCT/EP2013/069124, dated Dec. 6, 2013.

European Search Report corresponding to 13157226.5, dated Dec. 6, 2013.

"Commission Decision of May 8, 1996 establishing an inventory and a common nomenclature of ingredients employed in cosmetic products", Official Journal of the European Communities, L 132/1, Jun. 1, 1996 (Jun. 1, 1996), pp. 1, 2, 36, 48, 112, 115, 176, 222, 253, 279, 379, 384, 385, 476, 520.

Sutyagin et al, Phase and Physical State of Polymers, Chemistry of Physics and Polymers Textbook, 2003.

* cited by examiner

COMPOSITION AND PROCESS FOR SEMI-PERMANENT STRAIGHTENING OF THE HAIR

The present invention relates to a composition and a process for semi-permanent straightening of the hair.

BACKGROUND OF THE INVENTION

A known method for straightening curly or frizzy hair involves the use of straightening irons. The high temperature of the iron leads to a breakage of hydrogen bonds in the keratin of the hair, achieving a temporary straightening. The hydrogen bonds are formed again by the action of moisture, so that the hair reverts back to its original shape over the time because of air humidity, and the straightening effect vanishes after washing the hair.

The shape of the hair is largely determined by the disulfide bonds linking two cysteine moieties of the hair keratin. In order to achieve a more permanent shaping of the hair, known methods involve the cleavage of the disulfide bonds by the action of a sulfide- or thio group containing reducing agent. After the hair has been brought into the desired shape, new disulfide bonds are formed by applying an oxidizing agent such as hydrogen peroxide, thus fixing the shape of the hair. The use of such agents, however, may cause damage to the hair.

As an example for this kind of hair shaping treatment, reference is made to GB 1 416 564, describing reducing compositions comprising thioglycolates or thiolactates as reducing agents and fixing compositions comprising hydrogen peroxide as an oxidizing agent. The reducing compositions may further comprise a salt of an acid such as glyoxylic acid as a buffering agent.

As an alternative to the above-described two-step reduction and oxidation process, the disulfide bridges can be cleaved by the action of an alkaline agent such as sodium hydroxide at a pH of about 11 or higher. Under these conditions, the disulfide (or cystin) moiety can undergo a disproportionation reaction under the elimination of sulfur, and is cleaved into an alpha-beta-unsaturated dehydro-alanine moiety and a cysteine moiety. After the hair has been brought into the desired shape, the dehydro-alanin moieties and the cysteine moieties form thioether bonds and combine to lanthionine, stabilizing the straightened state of the hair. Since the disulfide or cystin moieties are converted into lanthionine moieties, this type of hair straightening process using an alkaline agent is also called lanthionization.

Both the two-stage reduction/oxidation method and the lanthionization method rely on a cleavage of the disulfide bonds and the formation of new bonds among the hair proteins, leading to an irreversible change of the shape of the hair. This means that these processes can achieve a permanent straightening, wherein the treated portion of the hair maintains its shape, and the straightening effect only vanishes because of the growth of the hair.

Recently, it has been found that carboxylic acids having a carbonyl group adjacent to the carboxy group, such as glyoxylic acid, which are known as a buffering agent in cosmetic compositions, may have a semi-permanent straightening effect when used in combination with mechanical straightening means.

In this respect, WO 2011/104282 describes a process for semi-permanent hair straightening, which involves applying a composition comprising an α-keto acid onto the hair, leaving the composition in contact with the hair for 15 to 120 minutes, drying the hair and straightening the hair with a straightening iron at a temperature of 200±50° C.

Furthermore, WO 2012/010351 describes a treatment for semi-permanent straightening of curly, frizzy or wavy hair by applying a solution of glyoxylic acid in combination with mechanical straightening, using a straightening iron at a temperature of 200±30° C. After the treatment, the hair is said to retain its shape for at least six consecutive washings.

EP 0685 219 describes a composition useful as a pre-treatment agent before subjecting the hair to a perm wave treatment, the composition comprising a film-forming cationic, anionic and/or amphoteric polymer, an amphoteric surfactant, an organic acid and a C2 to C4 alcohol, and being free of cationic surfactants.

SUMMARY OF THE INVENTION

The present invention provides a hair straightening composition having a pH of 4 or less and comprising:
 at least one carboxylic acid of the formula (I) and/or a hydrate thereof and/or a salt thereof, at a total concentration in the range of 0.1 to 40% by weight, based on the weight of the total composition:

R—CO—COOH                                  Formula (I)

wherein R is selected from hydrogen, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy; and
 at least one polymeric thickening agent selected from non-ionic, anionic, cationic and amphoteric polymers having a viscosity of at least 500 mPa·s, preferably 1,000 mPa·s, more preferably 1,500 mPa·s and more preferably 2,000 mPa·s (measured at a polymer concentration of 1% by weight in water at 20° C. with a Brookfield viscometer at 10 rpm for 1 minute with an appropriate spindle).

The composition may be formulated as a one-part composition, or as a two-part composition comprising the parts A and B, which are stored separately and mixed prior to the application to the hair, wherein part A comprises the carboxylic acid of formula (I) and part B comprises at least one of a fragrance, a surfactant or a conditioning component, and wherein the polymeric thickening agent is contained in either or both of part A and part B. Improved fragrance stability is observed with two-part compositions.

In another aspect, the present invention provides a process for semi-permanent hair straightening, comprising the following steps performed in this order:
(a) application of the hair straightening composition, which may be a one-part composition or a mixture of parts A and B of a two-part composition, as defined above, onto the hair;
(b) leaving the composition on the hair for 1 to 120 minutes;
(c) optionally rinsing off the hair;
(d) drying the hair;
(e) treating the hair with an iron having a surface temperature of 180±50° C.; and
(f) optionally rinsing off and/or shampooing the hair and drying.

Further aspects of the present invention relate to the use of the composition for straightening hair and to a kit for hair straightening, comprising the straightening composition and a straightening iron.

The hair straightening composition according the present invention may meet one of the following requirements (1), (2) or (1)+(2):

(1) the hair straightening composition does not contain a quaternary ammonium salt having two $C_5$-$C_{24}$ linear or branched, saturated or unsaturated hydrocarbon groups in the molecule, which may be the same or different and may be optionally substituted with one or more substituents selected from halogen, hydroxyl, amino and $C_1$-$C_4$ alkoxy;

(2) the hair straightening composition is not an aqueous solution of 13.0 wt. % of glyoxylic acid monohydrate (corresponding to 10.4 wt. % glyoxylic acid) and 1.6 wt. % of dehydoxanthan gum and having a pH of 1.5 (adjusted with NaOH);

DETAILED DESCRIPTION OF THE INVENTION

Carboxylic acids of the formula (I), such as glyoxylic acid, have recently been found to provide remarkable semi-permanent straightening effects. When the hair is treated with a straightening iron at high temperature after the application of the acid, however, there is the problem that excessive smoke development may occur. This problem has not yet been addressed in the prior art.

The present inventors have found that this problem can be solved by combining the carboxylic acid of formula (I) with a specific polymeric thickening agent, which also provides an improved hair feel during application.

1. The Carboxylic Acid of Formula (I)

The straightening composition comprises at least one carboxylic acid of the following formula (I) as the active component for achieving the straightening effect:

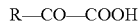
$$R\text{—}CO\text{—}COOH \qquad \text{Formula (I)}$$

wherein R is selected from hydrogen, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy.

As preferred examples, glyoxylic acid, pyruvic acid and 2-ketobutyric acid can be mentioned.

The carboxylic acid of Formula (I) may be comprised in the composition in its free acid form. The carbonyl group adjacent to the acid group of the acid may also be present in the hydrate form. Apart from the free acid form and the hydrate thereof, salts of the acid or the hydrate may also be used.

The hydrate of the acid of Formula (I) may be formed when providing the composition in an aqueous medium. For instance, glyoxylic acid (H—CO—COOH) in aqueous solution is almost quantitatively present as the hydrate (H—C(OH)$_2$—COOH). Besides, the hydrate may also condense to dimers.

A salt of the carboxylic acid of Formula (I) may also be used. As examples, alkali metal salts such as the sodium or potassium salt, alkaline earth metal salts such as the magnesium salt or the calcium salt and tertiary and quaternary ammonium salts may be mentioned.

In the present invention, glyoxylic acid, its salts and its hydrated form are the more preferred carboxylic acids of Formula (I).

The concentration of the at least one carboxylic acid of the Formula (I) and/or a hydrate thereof and/or salts thereof is in the range of 0.1 to 40%, preferably 0.5 to 40%, more preferably 2.5 to 40%, more preferably 0.5 to 30%, more preferably 1 to 25% and more preferably 2.5 to 20%, and even more preferably 2.5 to 14% by weight, based on the total weight of the straightening composition.

As discussed above, conventional permanent hair shaping/straightening techniques are based on the re-organization of the disulfide bridges and involve a cleavage of the disulfide bonds either by using a sulfur-based reducing agent or an alkali agent, followed by the shaping of the hair and the formation of new bonds (i.e., disulfide bonds formed by the action of an oxidizing agent or thioether bonds, respectively). In contrast to these permanent straightening methods, the present invention does not utilize cleavage of the disulfide bonds and fixing the bonds in the new shape. Therefore, the straightening composition of the present invention does not require the presence of sulfur-based reducing agents, and preferably is free of sulfur based reducing agents. However, up to 2% by weight calculated to the total of the composition of sulfur based reducing agents does not disturb the straightening performance of the composition. Therefore, the composition usually has less than 2% by weight of sulfur-based reducing agents, and preferably is free of sulfur-based reducing agents.

2. The Thickening Polymer

The straightening composition comprises at least one polymeric thickening agent selected from non-ionic, anionic, cationic and amphoteric polymers having a viscosity of at least 500 mPa·s measured at a polymer concentration of 1% by weight in water and at 20° C. with a Brookfield viscometer, e.g., at 10 rpm for 1 minute with an appropriate spindle.

The total concentration of the one or more thickening agent is typically within the range of 0.01 to 15 wt. %, preferably 0.05 to 10 wt. %, more preferable 0.1 to 5 wt. %, and more preferably 0.5 to 2 wt. % based on the weight of the straightening composition.

Non-Ionic Polymers

Any cosmetically acceptable non-ionic thickening polymers, which are usually employed in the field of hair cosmetic compositions, may be used as the polymeric thickening agent in the composition of the present invention. The composition may include a single kind or multiple kinds of non-ionic polymer, and may further include one or more anionic, cationic and/or amphoteric polymers in combination with the non-ionic polymer.

Examples for the non-ionic polymers include neutral polysaccharides and derivatives such as ethers or esters thereof. In this respect, neutral gums such as guar gum, hydroxypropyl guar, cellulose ethers such as hydroxyethylcellulose (HEC), methyl hydroxyethylcellulose (MHEC), ethyl hydroxyethylcellulose (EHEC), methyl ethyl hydroxyethylcellulose (MEHEC), hydroxypropylcellulose (HPC), hydroxypropylmethylcellulose (HPMC), hydrophobically modified derivatives thereof such as HM-EHEC, starch and dextrins may be mentioned.

Cellulose ethers such as MHEC or MEHEC are preferable. As commercially available example, STRUCTURE® CEL 12000 M (MEHEC) may be mentioned (available from AkzoNobel, the number indicating the viscosity in cps).

Anionic Polymers

Any cosmetically acceptable anionic thickening polymers, which are usually employed in the field of hair cosmetic compositions, may be used as the polymeric thickening agent in the composition of the present invention. The composition may include a single kind or multiple kinds of anionic polymer, and may further include one or more non-ionic, cationic and/or amphoteric polymers in combination with the anionic polymer.

Examples for the anionic polymer include anionic polysaccharides and derivatives thereof, such as alginate, pectin, hyaluronate, anionic gums such as xanthan gum, dehydroxanthan gum, hydroxypropyl xanthan gum, gum arabic, gum karaya or gum tragacanth, or anionic cellulose derivatives such as carboxymethyl cellulose (CMC).

Further examples include synthetic anionic polymers such as polyacrylic acid or copolymers containing acrylic acid in combination with neutral vinylic and/or acrylic monomers, and salts thereof such as sodium polyacrylate.

Xanthan gum, hydroxypropyl xanthan gum and dehydroxanthan gum are particularly preferable in view of pH stability.

Cationic Polymers

Any cosmetically acceptable cationic thickening polymers, which are usually employed in the field of hair cosmetic compositions, may be used as the polymeric thickening agent in the composition of the present invention. The composition may include a single kind or multiple kinds of cationic polymer, and may further include one or more non-ionic, anionic and/or amphoteric polymers in combination with the cationic polymer.

A cationic polymer is a polymer having a cationic group such as quaternary ammonium or a group capable of being ionized into a cationic group, such as a primary, secondary or tertiary amine group. The cationic polymer typically is a polymer containing an amine group or an ammonium group in a side chain of the polymer chain, or a polymer including a diallyl quaternary ammonium salt as a constituent unit.

Among the cationic polymers, polymers having tertiary amine groups or quaternary ammonium groups are preferable, and polymers having quaternary ammonium groups are more preferable, since these polymers are not prone to condensation with the carbonyl group of the carboxylic acid of Formula (I). Conversely, polymers having primary amine groups are less preferable, since they might undergo condensation reactions with the carboxylic acid of Formula (I) and thus reduce the effective concentration thereof.

Examples of preferred cationic polymers include cationized cellulose, cationic starch, cationic guar gum, a vinylic or (meth)acrylic polymer or copolymer having quaternary ammonium side chains, (meth)acrylate/aminoacrylate copolymer, amine substituted polyacrylate crosspolymers, a polymer or copolymer of a diallyl quaternary ammonium salt, and quaternized polyvinylpyrrolidone.

As an example of the vinylic or (meth)acrylic polymer or copolymer having quaternary ammonium side chains, poly (2-methacryloxyethyltrimethylammonium chloride) (Polyquaternium-37) may be mentioned.

Specific examples of the quaternized polyvinylpyrrolidone include quaternary ammonium salts synthesized from a copolymer of vinylpyrrolidone (VP) and dimethylaminoethyl methacrylate, and diethyl sulfate (polyquaternium-11).

As an example of the (meth)acrylate/aminoacrylate copolymer, Acrylates/Aminoacrylates/C10-30 Alkyl PEG-20 Itaconate Copolymer may be mentioned.

As an example of the amine substituted polyacrylate crosspolymers, Polyacrylates-1 Crosspolymer may be mentioned.

Specific examples of the cationized cellulose include a polymer of a quaternary ammonium salt obtained by adding glycidyltrimethylammonium chloride to hydroxyethylcellulose (polyquaternium-10), and a hydroxyethylcellulose/dimethyldiallylammonium chloride copolymer (polyquaternium-4), and a polymeric quaternary ammonium salt of hydroxyethyl cellulose reacted with a trimethyl ammonium substituted epoxide and a lauryl dimethyl ammonium substituted epoxide (polyquaternium-67).

Among these examples, polyquaternium-37 is particularly preferable.

Amphoteric Polymers

The amphoteric polymer contains both, cationic and anionic groups. From a structural point of view, the amphoteric polymer may be derived from any of the described cationic polymer types by the additional introduction of anionic groups or co-monomers.

Like the cationic polymers, the amphoteric polymers may also provide a hair conditioning effect, specifically in case of a positive net charge.

Any cosmetically acceptable amphoteric thickening polymers, which are usually employed in the field of hair cosmetic compositions, may be used as the polymeric thickening agent in the composition of the present invention. The composition may include a single kind or multiple kinds of amphoteric polymer, and may further include one or more non-ionic, anionic and/or cationic polymers in combination with the amphoteric polymer.

As examples for the amphoteric polymer, carboxyl-modified or sulfonate-modified cationic polysaccharides such as carboxymethylchitosan may be mentioned.

Further examples include copolymers of cationic vinylic or (meth)acrylic monomers with (meth)acrylic acid, such as dimethyldiallylammonium chloride/acrylic acid copolymer (polyquaternium-22).

As an amphoteric polymer, polyquaternium-22 is particularly preferable.

3. Surfactant

The straightening composition may comprise a surfactant. As the surfactant, any of a cationic surfactant, a nonionic surfactant, an amphoteric surfactant and an anionic surfactant can be used. It is also possible to use two or more types of surfactants in combination.

The cationic surfactant is preferably a mono-long chain alkyl quaternary ammonium salt, having a $C_8$-$C_{24}$ alkyl residue and three $C_1$-$C_4$ alkyl residues.

Preferably at least one mono alkyl quaternary ammonium surfactant is selected from the compounds with the general formula

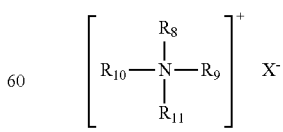

wherein $R_8$ is a saturated or unsaturated, branched or straight alkyl chain with 8-22 C atoms or

wherein $R_{12}$ is a saturated or unsaturated, branched or straight alkyl chain with 7-21 C atoms and n is an integer of 1-4, or

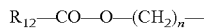
$R_{12}$—CO—O—$(CH_2)_n$— wherein $R_{12}$ is a saturated or unsaturated, branched or straight alkyl chain with 7-21 C atoms and n is an integer of 1-4, and $R_9$, $R_{10}$ and $R_{11}$ are independent from each other an alkyl group with 1 to 4 carbon atoms, hydroxyl alkyl chain with 1 to 4 carbon atoms, or ethoxy or propoxy group with a number of ethoxy or propoxy groups varying in the range of 1 to 4, and X is chloride, bromide, methosulfate or ethosulfate.

Suitable cationic surfactants are, for example, long-chain quaternary ammonium compounds which can be used alone or in admixture with one another, such as cetyl trimethyl ammonium chloride, myristyl trimethyl ammonium chloride, behentrimonium chloride, trimethyl cetyl ammonium bromide, stearyl trimethyl ammonium chloride, stearyl trimonium chloride and stearamidopropyltrimonium chloride.

Examples of the nonionic surfactant include polyoxy-$C_{1-4}$-alkylene $C_{8-24}$-alkyl ether, polyoxy-$C_{1-4}$-alkylene $C_{8-24}$-alkylene alkenyl ether, higher ($C_{12}$-$C_{24}$) fatty acid sucrose ester, polyglycerin $C_{8-24}$-fatty acid ester, higher ($C_{12}$-$C_{24}$) fatty acid mono- or diethanolamide, polyoxyethylene hardened castor oil, polyoxyethylene sorbitan $C_{8-24}$-fatty acid ester, polyoxyethylene sorbit $C_{8-24}$-fatty acid ester, $C_{8-24}$-alkyl saccharide surfactant, $C_{8-24}$-alkylamine oxide, and $C_{8-24}$-alkylamidoamine oxide.

Examples of the amphoteric surfactant include an imidazoline-based surfactant, a carbobetaine-based surfactant, an amidobetaine-based surfactant, a sulfobetaine-based surfactant, a hydroxysulfobetaine-based surfactant and an amidosulfobetaine-based surfactant.

Examples of the anionic surfactant include alkylbenzenesulfonate, alkyl or alkenyl ether sulfate, alkyl or alkenyl sulfate, olefin sulfonate, alkanesulfonate, saturated or unsaturated fatty acid salts, alkyl or alkenyl ether carboxylate, α-sulfo fatty acid salts, N-acylamino acid type surfactants, phosphoric acid mono- or diester type surfactants, and sulfosuccinate. Examples of the alkyl ether sulfate include polyoxyethylene alkyl ether sulfate. Examples of the counterion for the anionic residues of these surfactants include an alkalimetal ion such as sodium ion or potassium ion; an alkaline earth metal ion such as calcium ion or magnesium ion; an ammonium ion; and an alkanolamine having 1 to 3 alkanol groups each having 2 or 3 carbon atoms (for example, monoethanolamine, diethanolamine, triethanolamine, or triisopropanolamine).

The surfactant can be used singly or in combination of two or more kinds. When adding a surfactant to the straightening composition, the content thereof usually is 0.05 to 10% wt. %, more preferably 0.1 to 5 wt. %, based on the total weight of the straightening composition.

4. Conditioning Component

The straightening composition may optionally comprise a conditioning component suitable for application to the hair. The conditioning component generally is an oil or an additional polymer which adheres to the hair and improves the feel and the manageability.

When using the conditioning component, the total content thereof is preferably 0.01 to 30 wt. %, more preferably 0.05 to 20 wt. %, and even more preferably 0.1% to 10 wt. %, based on the total weight of the straightening composition.

Examples of the conditioning component generally include silicones, higher alcohols, and organic conditioning oils (for example, hydrocarbon oil, polyolefin and fatty acid ester), as well as cationic surfactants and cationic or amphoteric polymers, including the ones described above.

The composition may comprise a single type of conditioning component, or two or more in combination.

Silicones

In order to improve the feel of use, the straightening composition preferably contains a silicone. Examples of the silicone include dimethylpolysiloxane, and modified silicone (for example, amino-modified silicone, fluorine-modified silicone, alcohol-modified silicone, polyether-modified silicone, epoxy-modified silicone, polyoxazoline silicone (as described in JP A 2-276824), or alkyl-modified silicone), but dimethylpolysiloxane, polyether-modified silicone and amino-modified silicone are preferred.

The dimethylpolysiloxane may be any cyclic or non-cyclic dimethylsiloxane polymer, and examples thereof include SH200 series, BY22-019, BY22-020, BY11-026, B22-029, BY22-034, BY22-050A, BY22-055, BY22-060, BY22-083, FZ-4188 (all by Dow Corning Toray Co., Ltd.), KF-9008, KM-900 series, MK-15H, and MK-88 (all by Shin-Etsu Chemical Co., Ltd.).

The polyether-modified silicone may be any silicone having a polyoxyalkylene group, and the group constituting the polyoxyalkylene group may be an oxyethylene group or an oxypropylene group. More specific examples include KF-6015, KF-945A, KF-6005, KF-6009, KF-6013, KF-6019, KF-6029, KF-6017, KF-6043, KF-353A, KF-354A, KF-355A (all by Shin-Etsu Chemical Co., Ltd.), FZ-2404, SS-2805, FZ-2411, FZ-2412, SH3771M, SH3772M, SH3773M, SH3775M, SH3749, SS-280X series, BY22-008 M, BY11-030, and BY25-337 (all by Dow Corning Toray Co., Ltd.).

The amino-modified silicone may be any silicone having an amino group or an ammonium group, and examples thereof include an amino-modified silicone oil having all or a part of the terminal hydroxyl groups capped with a methyl group or the like, and an amodimethicone which does not have the terminals capped. A preferred example of the amino-modified silicone may be a compound represented by the following formula:

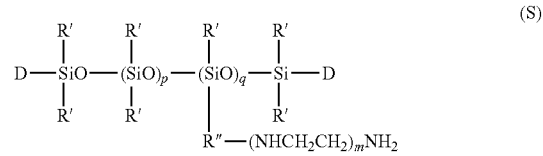

(S)

wherein R' represents a hydroxyl group, a hydrogen atom or $R^X$; $R^X$ represents a substituted or unsubstituted monovalent hydrocarbon group having 1 to 20 carbon atoms; D represents $R^X$, R"—$(NHCH_2CH_2)_mNH_2$, $OR^X$, or a hydroxyl group; R" represents a divalent hydrocarbon group having 1 to 8 carbon atoms; m represents a number from 0 to 3; p and q represent numbers, the sum of which is, as a number average, equal to or greater than 10 and less than 20,000, preferably equal to or greater than 20 and less than 3000, more preferably equal to or greater than 30 and less than 1000, and even more preferably equal to or greater than 40 and less than 800.

Specific examples of suitable commercially available products of the amino-modified silicone include amino-modified silicone oils such as SF8452C, SS-3551 (all by Dow Corning Toray Co., Ltd.), KF-8004, KF-867S, and KF-8015 (all by Shin-Etsu Chemical Co., Ltd.); and amodimethicone emulsions such as SM8704C, SM8904, BY22-079, FZ-4671, and FZ-4672 (all by Dow corning Toray Co., Ltd.).

The total content of these silicones in the straightening composition of the present invention is usually 0.1 to 20 wt. %, preferably 0.2% to 10 wt. % and more preferably 0.5 to 5 wt. %, based on the total weight of the straightening composition.

Oil Component

For improving the feel upon use, the straightening composition may also include an organic conditioning oil. The organic conditioning oil that is suitably used as a conditioning component is preferably a low-viscosity and water-insoluble liquid, and is selected from a hydrocarbon oil having at least 10 carbon atoms, a polyolefin, a fatty acid ester, a fatty acid amide, a polyalkylene glycol, and mixtures thereof. The viscosity of such an organic conditioning oil as measured at 40° C. is preferably 1 to 200 mPa·s, more preferably 1 to 100 mPa·s, and even more preferably 2 to 50 mPa·s. For the determination of the viscosity, a capillary viscometer may be used.

Examples of the hydrocarbon oil include a cyclic hydrocarbon, a linear aliphatic hydrocarbon (saturated or unsaturated), and a branched aliphatic hydrocarbon (saturated or unsaturated), and polymers or mixtures thereof are also included. The linear hydrocarbon oil preferably has 12 to 19 carbon atoms. The branched hydrocarbon oil includes hydrocarbon polymers, and preferably has more than 19 carbon atoms.

The polyolefin is a liquid polyolefin, more preferably a liquid poly-α-olefin, and even more preferably a hydrogenated liquid poly-α-olefin. The polyolefin used herein is prepared by polymerizing an olefin monomer having 4 to 14 carbon atoms, and preferably 6 to 12 carbon atoms.

The fatty acid ester may be, for example, a fatty acid ester having at least 10 carbon atoms. Examples of such a fatty acid ester include esters having a hydrocarbon chain derived from a fatty acid and an alcohol (for example, monoesters, polyhydric alcohol esters, or di- and tricarboxylic acid esters). The hydrocarbon group of these fatty acid esters may have another compatible functional group such as an amide group or an alkoxy group as a substituent, or the hydrocarbon group may be covalently bonded to those functional groups. More specifically, an alkyl and alkenyl ester of a fatty acid having a fatty acid chain having 10 to 22 carbon atoms, a carboxylic acid ester of an aliphatic alcohol having an aliphatic chain derived from an alkyl and/or alkenyl alcohol having 10 to 22 carbon atoms, and a mixture thereof are suitably used. Specific examples of these preferred fatty acid esters include isopropyl isostearate, hexyl laurate, isohexyl laurate, isohexyl palmitate, isopropyl palmitate, isopropyl myristate, decyl oleate, isodecyl oleate, hexadecyl stearate, decyl stearate, dihexadecyl adipate, lauryl lactate, myristyl lactate, cetyl lactate, oleyl stearate, oleyl oleate, oleyl myristate, lauryl acetate, cetyl propionate and dioleyl adipate.

Further suitable oil components are natural oils such as paraffin oil and natural triglycerides.

Suitable natural triglycerides are argan oil, shea butter oil, karite oil, olive oil, almond oil, avocado oil, ricinus oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, passiflora oil, black cumin oil, borage oils, grapeseed oil, hempseed oil, kukui nut oil, and rosehip oil.

The organic conditioning oil may be used in combination of two or more kinds, and the total concentration is typically in the range of 0.1 to 20 wt. %, preferably 0.2 to 10 wt. %, more preferably 0.5 to 5 wt. %, based on the total weight of the straightening composition.

Alcohols

From the viewpoint of improving the sense of touch and stability, the straightening composition may also contain a higher alcohol having 8 carbon atoms or more. Usually, the higher alcohol has 8 to 22 carbon atoms, and preferably 16 to 22 carbon atoms. Specific examples thereof include cetyl alcohol, stearyl alcohol, behenyl alcohol, and mixtures thereof.

The higher alcohol may be used in combination of two or more kinds, and the content thereof is typically 0.1 to 20 wt. %, preferably 0.2 to 10 wt. %, more preferably 0.5 to 5 wt. %, based on the total weight of the straightening composition.

Additionally polyols may suitably be comprised in the compositions. Examples of the polyalkylene glycol include polyethylene glycol and polypropylene glycol, and a mixture of the two may be used, or a copolymer of ethylene oxide and propylene oxide may also be used.

5. Formulation of the Straightening Composition

The straightening composition of the present invention may suitably be in the form of a thickened solution or gel, emulsion, cream, paste and mousse.

The overall viscosity of the composition generally depends on the type and amount of the polymeric thickening agent and usually is at least 1000 mPa*s, as measured at 20° C. with a Brookfield viscometer, under conditions such as 10 rpm for 1 minute with an appropriate spindle. If the composition is provided in the form of a thickened solution, gel or emulsion, the viscosity is typically within the range of 1,000 to 25,000, preferably 2,500 to 15,000 mPa*s.

In order to provide a sufficient straightening effect, the pH of the straightening composition is 4.0 or less, preferably in the range of 1 to 3.5, more preferably 1 to 3 and more preferably 1.5 to 3, as measured directly and at ambient temperature (25° C.). The pH of the composition may be adjusted using known alkaline solutions, preferably with sodium hydroxide solution.

Gel Formulations

A preferable straightening composition may be formulated as a gel comprising the following ingredients:

(Gel Formulation 1)

| % by weight | |
|---|---|
| 2 to 20 | Glyoxylic acid; |
| 0.1 to 2 | Anionic thickening polymer, preferably xanthan or hydroxypropyl xanthan or dehydroxanthan; |
| 0.1 to 1 | surfactant such as cocamidopropylbetaine or cocoyl betaine, decyl glucoside, sodium laureth sulphate |

Alternative preferable gel formulations are described below.

(Gel Formulation 2)

| % by weight | |
|---|---|
| 2 to 20 | Glyoxylic acid; |
| 0.1 to 2 | Non-ionic thickening polymer, preferably MHEC or MEHEC; |

-continued

| % by weight | |
|---|---|
| 0.1 to 1 | surfactant such as cocamidopropylbetaine or cocoyl betaine, decyl glucoside, sodium laureth sulphate, or cetrimonium chloride |

(Gel Formulation 3)

| % by weight | |
|---|---|
| 2 to 20 | Glyoxylic acid; |
| 0.1 to 2 | cationic thickening polymer, preferably polyquaternium-37; |
| 0.1 to 1 | surfactant such as cocamidopropylbetaine or cocoyl betaine, decyl glucoside or cetrimonium chloride |

(Gel Formulation 4)

| % by weight | |
|---|---|
| 2 to 20 | Glyoxylic acid; |
| 0.1 to 2 | amphoteric thickening polymer, preferably polyquaternium-22; |
| 0.1 to 1 | surfactant such as cocamidopropylbetaine or cocoyl betaine, decyl glucoside, sodium laureth sulphate, or cetrimonium chloride |

The gel formulations 1-4 may optionally comprise additional ingredients such as surfactants and/or conditioning components. Cosmetically acceptable additives such as preservatives, dyes, and fragrances may be added if desired. The balance is water. The pH of the gel formulations 1-4 may be adjusted to 1.5 to 2.5 using a base such as sodium hydroxide, if necessary.

The viscosity of the gel formulations 1-4 depends on the type and amount of the thickening polymer and is typically within the range of 1,000 to 25,000, preferably 2,500 to 15,000 mPa*s, as measured at 20° C. with a Brookfield viscometer, under conditions such as 10 rpm for 1 minute with an appropriate spindle.

Emulsions

For further enhancing the ease of use, it is also possible to formulate the straightening composition as an emulsion. Preferable emulsions are gel emulsions which contain the same ingredients in the same amounts as the Gel Formulations 1-4 described above, and additionally include a fatty alcohol, optionally in combination with a surfactant, preferably a cationic surfactant and/or an oil component, preferably a silicone. An especially preferable emulsion formulation is described in the following.

(Emulsion Formulation 1)

| 2 to 20 wt. % | Glyoxylic acid; |
|---|---|
| 0.1 to 2 wt. % | Anionic thickening polymer, preferably xanthan, hydroxypropyl xanthan or dehydroxanthan; |
| 1-5 wt. % | Fatty Alcohol, preferably cetearyl alcohol |
| 1-5 wt. % | $C_{12-24}$-alkyltrimethlyammonium salt, such as behentrimonium chloride |

The emulsion formulation 1 may optionally comprise additional ingredients such as surfactants and/or conditioning components. Cosmetically acceptable additives such as preservatives, dyes, and fragrances may be added if desired. The balance is water. The pH of the emulsion formulation 1 may be adjusted to 1.5 to 2.5 using a base such as sodium hydroxide, if necessary.

Two-Component Formulations

In case it is desired to include compounds such as fragrances or surfactants and/or conditioning components which comprise ester moieties or other acid-sensitive groups, it is possible that the storage stability at the above-described pH values is diminished. Besides, it is also possible that fragrance compounds undergo undesired reactions with the carbonyl group of the carboxylic acid of formula (I), which may lower the storage stability.

In order to avoid such problems, it may be preferable in these cases to formulate the straightening composition as a two-part system, comprising the parts A and B, which are stored separately and mixed prior to the application to the hair.

Part A comprises the carboxylic acid of the formula (I), while part B comprises at least one of a fragrance, a surfactant and a conditioning agent. The thickening agent and, optionally, acid insensitive surfactants and conditioning agents may be added to part A, to part B or to both parts.

The fragrance may use fragrance raw materials described in Common Fragrance and Flavor Materials: Preparation, Properties and Uses, by Horst Surburg, Johannes Panten (John Wiley & Sons, 5th edition, 2006), Perfume and Flavor Chemicals, volume 1 and 2, by Steffen Arctander, (published by the author in 1969), Perfume and Flavor Materials of Natural Origin, by Steffen Arctander (published by the author in 1961).

In the view of stability, the fragrance is preferably a citrus note, more preferably one or more fragrance raw materials having a citrus note, selected from Limonene, Pinene, Citral, Dihydromyrcenol, Pamplefleur, Lemon oil, Orange oil, Mandarin oil and Lime oil. The content of the fragrance raw materials having a citrus note is preferably 5-100%, more preferably 20-90%, even more preferably 30-80%, of the fragrance.

In the view of the same reason, the Part A is preferably comprised of a fragrance having a citrus note, more preferably one or more fragrance raw materials having a citrus note, selected from Limonene, Pinene, Citral, Dihydromyrcenol, Pamplefleur, Lemon oil, Orange oil, Mandarin oil and Lime oil.

The pH of part B is adjusted such that the ingredients have sufficient storage stability, typically above 4 and usually within the range of 4 to 8, while the pH of part A is less than 4, usually within the range of 1 to 3.5. The final pH after mixing of parts A and B is 4 or lower, preferably 1 to 3.5.

Preferable two-component formulations are described in the following.

Two-Component Formulation 1 (Gel)
Part A: Gel Component Comprising Glyoxylic Acid

| 5-40 wt. % | Glyoxylic acid; |
|---|---|
| 0.2 to 4 wt. % | Anionic thickening polymer, preferably xanthan, dehydroxanthan or hydroxypropyl xanthan |

Acid-insensitive components may be added if desired. The balance is water, and the pH may be adjusted to pH 1-3, preferably 1.5 to 2, with a base such as NaOH, if necessary.

Part B: Conditioning Component Comprising an Ester Compound and/or Fragrance

| 1-4 wt. % | Fatty acid ester, preferably isopropyl palmitate or isopropyl myristate |

-continued

| | |
|---|---|
| 2-8% | PEG-40-hydrogenated castor oil |
| 0-2% | Fragrance |

Further ingredients such as surfactants or additional conditioning components may be added if desired. The balance is water. The pH is 6-7.

The parts A and B are stored separately and are mixed at a predefined ratio such as 1:1 prior to use.

Two-Component Formulation 2 (Gel-Emulsion)

Part A: Gel Component Comprising Glyoxylic Acid

| | |
|---|---|
| 5-40 wt. % | Glyoxylic acid; |
| 0.2 to 4 wt. % | Anionic thickening polymer, preferably xanthan or dehydroxanthan or hydroxypropyl xanthan |

Acid-insensitive components may be added if desired. The balance is water, and the pH may be adjusted to pH 1-3, preferably 1.5 to 2, with a base such as NaOH, if necessary.

Part B: Conditioning Component in Emulsion Form Comprising an Ester Compound and/or Fragrance

| | |
|---|---|
| 1-8 wt. % | Fatty alcohol, preferably cetearyl alcohol |
| 1-8 wt. % | silicone oil |
| 1-8 wt. % | $C_{12-24}$-alkyltrimethlyammonium salt, such as behentrimonium chloride |
| 0.5-4 wt. % | Fatty acid ester, preferably isopropyl palmitate or isopropyl myristate |
| 0-2% | Fragrance |

Further ingredients such as surfactants or additional conditioning components may be added if desired. The balance is water. The pH is 6-7.

The Parts A and B are stored separately and are mixed at a predefined ratio such as 1:1 prior to use.

6. Hair Treatment Process

The hair treatment process of the present invention achieves a semi-permanent straightening of the hair, utilizing the acid of formula (I) such as glyoxylic acid as the active agent. The straightening effect of this process is not achieved by cleaving the disulfide bonds by reduction or the action of strong alkali. Accordingly, the usage of a reducing composition or an alkaline relaxer (lanthionization agent) is not required.

In step (a) of the process of the present invention, the straightening composition is applied to the hair. The application weight ratio of hair to composition is 0.5:2 to 2:0.5, preferably 0.5:1 to 1:0.5, more preferably about 1:1.

Subsequent to the application, the straightening composition is left on the hair for 1 to 120 minutes, preferably 5 to 90 minutes, more preferably 10 to 60 minutes and more preferably 15 to 45 minutes at a temperature of 45° C. or below, preferably at ambient temperature (step (b)). Then, the straightening composition is optionally rinsed off from hair (step (c)).

In subsequent step (d), the hair is dried in order to avoid an excessive steam generation in the subsequent step of treating the hair with the iron. Typically, a hair dryer is used for this purpose. It is preferable to dry the hair under continuous combing in order to prevent entanglement of the hair. Subsequent to the drying, the hair is treated with an iron having a surface temperature of 180±50° C., preferably 170 to 200° C. A usual straightening iron may be used for this purpose (step (e)). Finally, the hair may optionally be rinsed off with water and/or shampooed and dried again (step (f)).

EXAMPLES

The present invention is now illustrated by the following non-limiting examples. The amounts of the ingredients are indicated as percent by weight.

Reference Example

A straightening composition in emulsion form was prepared by mixing the following ingredients:

| Ingredients | wt. % |
|---|---|
| Glyoxylic Acid 50% | 20 |
| Cetearyl Alcohol | 2.0 |
| Behentrimonium Chloride | 2.0 |
| NaOH | q.s. pH 2 |
| Water | ad. 100 |

Example 1

A straightening composition in gel form was prepared by mixing the following ingredients:

| Ingredients | wt. % |
|---|---|
| Glyoxylic Acid 50% | 20 |
| Dehyroxanthan Gum | 1.0 |
| NaOH | q.s. pH 2 |
| Water | ad. 100 |

Example 2

A straightening composition in gelled emulsion form was prepared by mixing the following ingredients:

| Ingredients | wt. % |
|---|---|
| Glyoxylic Acid 50% | 20 |
| Dehyroxanthan Gum | 1.0 |
| Cetearyl Alcohol | 2.0 |
| Behentrimonium Chloride | 2.0 |
| NaOH | q.s. pH 2 |
| Water | ad. 100 |

Test Example 1

A hairstreak weighing approximately 2 g was shampooed with a commercially available shampoo and blow dried. Subsequently, it was treated with approximately 1 g of a straightening composition, left at room temperature for about 15 min and dried with a hair drier. Afterwards, the hairstreak was treated with a flat iron having a surface temperature of 220° C. for 6 times. Smoke generation and iron gliding on the hair surface were observed during ironing. The streaks were then evaluated for their coated/uncoated feeling by a hair stylist visually and/or subjectively. The performance of the composition of the Reference Example and of Examples 1 and 2 of the present invention was evaluated with respect to smoke generation and ease/feel of use. The results are shown in Table 1 below.

TABLE 1

Results of comparative tests

| | Reference Example | Example 1 | Example 2 |
|---|---|---|---|
| Low Smoke Generation (during step e) | 4 | 2 | 2 |
| Good Iron Gliding (during step e) | 3 | 4 | 1 |
| Uncoated Hair Feeling (after step e) | 4 | 2 | 2 |

5 = very poor result; 4 = poor; 3 = satisfactory; 2 = good; 1 = very good result As apparent from the results, the compositions of Examples 1 and 2 according to the present invention provide a substantial reduction of the smoke generation during the ironing, and also are advantageous in view of hair feeling during application. The emulsion formulations of the Reference Example and Example 2 facilitate the gliding of the iron, in comparison to the plain gel formulation of Example 1. In Example 2, the gliding is remarkably improved.

Example 3: Two-Component Gel-Emulsion

Part A: Gel Component (pH 1.5)

| Ingredients | wt. % |
|---|---|
| Glyoxylic Acid 50% | 40 |
| Dehyroxanthan Gum | 1.0 |
| NaOH 32% | 3.0 |
| Water | ad. 100 |

Part B: Emulsion Component (pH 6.5)

Five variants of Part B differing with respect to the fragrance were prepared (no fragrance, fragrance A-D).

| Ingredients | wt. % |
|---|---|
| Cetearyl Alcohol | 2.0 |
| Silicone emulsion | 2.0 |
| Behentrimonium Chloride | 1.5 |
| Fragrance* | 0 or 1.0 |
| Isopropyl myristate | 1.0 |
| Dipropylene glycol | 1.0 |
| Water | ad. 100 |

*Fragrances A-D: see the Table below.

The parts A and B were mixed at a ratio of 1:1, yielding a mixed gel-emulsion composition having a pH of 1.6-1.7.

Test Example 2

The storage stability of the parts A and B of Example 3 and of the mixed gel emulsion were evaluated by comparing the scent of the fresh mixture, the mixture stored for one month at 50° C. and the mixture of the components stored separately for one month at 50° C. Several variants of Part B were examined, differing with respect to the fragrance component. Fragrance evaluation was done by the group of trained technicians. The following results were obtained as in the Table 2.

TABLE 2

Comparative test results of fragrance stability

| | | After one month stored at 50° C. | |
|---|---|---|---|
| Fragrance of Part B | Fresh Sample | Mixture stored | Parts A and B stored separately |
| None | 3 | 5 | 3 |
| Fragrance A*[1] | 1 | 6 | 3 |
| Fragrance B*[2] | 1 | 5 | 1 |
| Fragrance C*[3] | 1 | 5 | 2 |
| Fragrance D*[4] | 1 | 5 | 2 |

Evaluation of Scent:

1 = very good; 2 = good; 3 = satisfactory; 4 = acceptable; 5 = unacceptable; 6 = bad

*[1]Copacabana ™ (Source: Mane; sweet, fruity odor)

*[2]Midnight Dream ™ (Source: Fragrance Resources; citric, soap-like odor)

*[3]Sensational Hair ™ (Source: Fragrance Resources; spice odor)

*[4]Parati ™ (Source: Mane; sweet, fruity odor)

Example 4: Two-Component Gel System

Part A: Gel Component (pH 1.5)

| Ingredients | wt. % |
|---|---|
| Glyoxylic Acid 50% | 40 |
| Dehyroxanthan Gum | 1.0 |
| NaOH 32% | 3.0 |
| Water | ad. 100 |

Part B: Conditioning Component Containing an Ester (pH 5-7)

Two variants of Part B were prepared, comprising isopropyl palmitate and isopropyl myristate as an ester component, respectively.

| Ingredients | wt. % |
|---|---|
| Ester component | 1.0 |
| PEG-40-hydrogenated castor oil | 1.0 |
| Water | ad 100 |

The parts A and B were mixed at a ratio of 1:1, yielding a mixed gel composition having a pH of 1.6-1.7.

Test Example 3

The impact on storage stability was evaluated by comparing the hair properties and the gliding of the iron with respect to natural hair and bleached hair either for the fresh mixture of Parts A and B of Example 4 or for a mixture aged for three days at 40° C. The hair streaks were treated in the same way as described above for Test Example 1, and subsequently rinsed and dried. The following results were obtained as presented in Table 3.

TABLE 3

Comparative test results on the effect of stability of the composition on straightening process

| Effect on hair | Fresh Mixture | | Mixture stored for 3 days at 40° C. | | Parts A and B stored separately for 3 days at 40° C., then mixed | |
|---|---|---|---|---|---|---|
| | Natural hair | Bleached hair | Natural hair | Bleached hair | Natural hair | Bleached hair |
| Softness* | 1 | 3 | 2 | 4 | 1 | 3 |
| Smoothness* | 1 | 3 | 2 | 4 | 1 | 3 |
| Gliding of the iron (step e) | 2 | 3 | 3 | 4 | 2 | 3 |

*Touch after treatment (after step f, rinsed out and dried)

Evaluation scale:
1 = very good;
2 = good;
3 = satisfactory;
4 = acceptable;
5 = unacceptable;
6 = bad

Example 5

| | % by weight |
|---|---|
| Glyoxylic acid | 5 |
| Polyquaternium-37 | 0.7 |
| Steartrimonium chloride | 1.5 |
| Dimethicone | 1.0 |
| Water | to 100 |

The pH of the example is 1.8.

Example 6

| | % by weight |
|---|---|
| Glyoxylic acid | 10 |
| Hxdroxyethylcellulose | 1.1 |
| Sodium hydroxide | q.s. to pH 1.9 |
| Behentrimonium chloride | 1.5 |
| Cocamide MEA | 0.5 |
| Dimethicone | 1.0 |
| Fragrance | 0.8 |
| Water | to 100 |

Example 7

| | % by weight |
|---|---|
| Glyoxylic acid | 10 |
| Xanthan gum | 0.7 |
| Sodium hydroxide | q.s. to pH 1.8 |
| Cocamide MEA | 1.5 |
| PEG-40 hydrogenated castor oil | 0.5 |
| Dimethicone | 1.0 |
| Fragrance | 0.8 |
| Water | to 100 |

Example 8

| | % by weight |
|---|---|
| Glyoxylic acid | 10 |
| Polyquaternium-22 | 0.7 |
| Sodium hydroxide | q.s. to pH 2.0 |
| Cetrimonium chloride | 1.5 |
| Dimethicone | 1.0 |
| PEG-40 hydrogenated castor oil | 0.5 |
| Fragrance | 0.8 |
| Water | to 100 |

Example 9

| | % by weight |
|---|---|
| Glyoxylic acid | 10 |
| Polyacrylate-1 cross polymer | 1 |
| Sodium hydroxide | q.s. to pH 1.5 |
| Dimethicone | 1.0 |
| PEG-40 hydrogenated castor oil | 0.5 |
| Fragrance | 0.8 |
| Water | to 100 |

Example 10

| | % by weight |
|---|---|
| Glyoxylic acid | 10 |
| Structure Plus ™ (product of Akzo Nobel) | 1 |
| Sodium hydroxide | q.s. to pH 1.5 |
| Dimethicone | 1.0 |
| PEG-40 hydrogenated castor oil | 0.5 |
| Fragrance | 0.8 |
| Water | to 100 |

Example 11

|  | % by weight |
| --- | --- |
| Glyoxylic acid | 10 |
| Polyquaternium-67 | 1 |
| Sodium hydroxide | q.s. to pH 1.5 |
| Dimethicone | 1.0 |
| PEG-40 hydrogenated castor oil | 0.5 |
| Fragrance | 0.8 |
| Water | to 100 |

The invention claimed is:

1. A process for semi-permanent hair straightening, comprising the following steps performed in this order:
   (a) application of a hair straightening composition;
   (b) leaving the composition on the hair for 10 to 60 minutes;
   (c) optionally rinsing off the hair;
   (d) drying the hair;
   (e) treating the hair with an iron having a surface temperature of 180±50° C., and
   (f) optionally rinsing off and/or shampooing the hair and drying,
   wherein the hair straightening composition has a pH of 1 to 3 and is an emulsion comprising:
   glyoxylic acid and/or a hydrate thereof and/or a salt thereof, at a total concentration in the range of 2.5 to 25% by weight, based on the weight of the total composition;
   at least one polymeric thickening agent having a viscosity of at least 500 mPa measured at a polymer concentration of 1% by weight, in water and at 20° C. with a Brookfield viscometer, wherein the polymeric thickening agent is an anionic polymer,
   a cationic surfactant; and
   at least one higher alcohol having 8 to 22 carbon atoms,
   wherein the combination with the application of a reducing composition or an alkaline relaxer is excluded.

2. The process of claim 1, wherein the hair is treated with an iron having a surface temperature of 170 to 200° C.

3. The process according to claim 1, wherein the hair straightening composition is a two-part composition comprising the parts A and B, which are provided for separate storage and for mixing prior to the application to the hair,
   wherein part A comprises glyoxylic acid and/or a hydrate thereof and/or a salt thereof, and part B comprises at least one of a fragrance, a cationic surfactant or a conditioning component, and
   wherein the polymeric thickening agent is contained in either or both of part A and part B.

4. The process according to claim 3, wherein the fragrance is one or more fragrance raw materials having citric note, selected from Limonene, Pinene, Citral, Dihydromyrcenol, Pamplefleur, Lemon oil, Orange oil, Mandarin oil and Lime oil.

5. The process according to claim 1, wherein the polymeric thickening agent is an anionic polymer selected from xanthan gum, hydroxypropyl xanthan gum and dehydro xanthan gum.

6. The process according to claim 1, wherein the hair straightening composition further comprises a silicone.

* * * * *